United States Patent [19]

Narayanan et al.

[11] Patent Number: 5,653,965
[45] Date of Patent: Aug. 5, 1997

[54] LOW VOC, SUNSCREEN SPRAY COMPOSITION CONTAINING A HYDROPHOBIC, FILM-FORMING POLYMER

[75] Inventors: Kolazi S. Narayanan, Wayne; Robert M. Ianniello, Oak Ridge; Edward G. Malawer; Ronald H. Goehner, Jr., both of Wayne, all of N.J.; James P. Cullen, Bartonville, Pa.

[73] Assignee: ISP Investments Inc., Wilmington, Del.

[21] Appl. No.: 505,090

[22] Filed: Jul. 21, 1995

[51] Int. Cl.⁶ .................. A61K 7/42; A61K 31/74; A01N 25/06

[52] U.S. Cl. .............. 424/59; 424/78.02; 424/78.08; 424/78.17; 424/400; 424/405

[58] Field of Search ................ 424/59, 60, 78.02, 424/78.08, 78.17, 400, 405

[56] References Cited

U.S. PATENT DOCUMENTS 5,208,011  5/1993  Vaughan ...................... 424/59

*Primary Examiner*—Shelley A. Dodson
*Attorney, Agent, or Firm*—Walter Katz; Marilyn J. Maue; Joshua J. Ward

[57] ABSTRACT

Stable, water-based formulations containing high levels of water insoluble UV protectants/insecticides are provided herein as sprayable microemulsions containing a film-forming polymer, e.g. Agrimer® VEMA ES 425 [poly (methyl vinyl ether-maleic acid monobutyl ester)]. The polymers are solubilized either by partial neutralization with a base, or by emulsification with appropriate emulsifiers. These formulations produce single phase, micro- or mini-emulsions (particle size<1 micron) on dilution with water. The formulations are useful as UV protectants in veterinary use, for protection of UV-labile insecticides, and for "pour on" applications.

5 Claims, No Drawings

LOW VOC, SUNSCREEN SPRAY COMPOSITION CONTAINING A HYDROPHOBIC, FILM-FORMING POLYMER

BACKGROUND OF THE INVENTION

1. Field of the Invention

This invention relates to low VOC sunscreen spray compositions, and, more particularly to subcompositions containing hydrophobic, film-forming polymer.

2. Description of the Invention

Stable microemulsions/microdispersions containing UV protectants and film-forming, water-insoluble polymers are available as UV protectant formulations for protecting UV labile active ingredients. These systems are based on N-alkyl pyrrolidones and long chain alkylolefin grafted polyvinyl pyrrolidones, and a UV protectant [e.g. octyl dimethyl para amino benzoate (Escalol® 507) hydroxy methoxy benzophenone (Escalol® 567), etc.]. However, there is a need for "pour on" compositions, to be used on animals, that will produce excellent wetting and spreading on hydrophobic surfaces with very little skin penetration, and which will offer high stability for the dispersed active ingredients, and, preferably including a film-former that would encapsulate the active ingredient.

SUMMARY OF THE INVENTION

Stable, water-based formulations containing high levels of water insoluble UV protectants/insecticides are provided herein as sprayable microemulsions containing a film-forming polymer, e.g. Agrimer® VEMA ES 425 [poly (methyl vinyl ether-maleic acid monobutyl ester)]. The polymers are solubilized either by partial neutralization with a base, or by emulsification with appropriate emulsifiers. These formulations produce single phase, micro- or mini-emulsions (particle size<1 micron) on dilution with water. The formulations are useful as UV protectants in veterinary use, for protection of UV-labile insecticides, and for "pour on" applications.

DETAILED DESCRIPTION OF THE INVENTION

MATERIALS AND METHODS

Materials

The invention formulations were prepared as single phase systems using alcohol/water medium, selective emulsifiers [alkylphenyl ethoxylates (Igepal CO)/ethoxylated glyceryl isostearates (Tagat)], and Agrimer VEMA ES type polymers as film-formers. Homogeneous compositions were obtained by stirring with a mechanical stirrer for a period of one hour. The samples were further tested for phase separation by centrifuging in a laboratory centrifuge for 45 minutes at 900 rpm.

Particle Size Measurements

Emulsion droplets were analyzed via an optical microscope, model Nikon S-Kt at 250×magnification. Particle size distribution for aqueous dispersions and emulsions were measured using a Microtrac particle size analyzer. Microemulsion range particle size distributions were measured using Leeds Northrup, Microtrac ultrafine particle analyzer, containing software package for data analysis.

Spectral Data

UV spectra were obtained by using Perkin Elmer UV/visible spectrophotometer model 559 A, Varian Cary 2300 and quartz cuvettes. Spectral grade solvents were used for dilution and preparing standard solutions.

Surface Properties Measurements

Static surface tension was measured using the ring method with a Fisher surface tensiomat. Dynamic surface tension was measured for several bubble frequencies using a Kruss BP 10 maximum bubble pressure tensiometer. Contact angle was measured using Kruss droplet analyzer, Model ACAMS-40 with attached computer software for image analysis. Wetting time was measured using Drave's cotton skein test. ASTM, 1990. The spreading of droplets was measured by measuring the area of the droplet compared to standards and expressing the area as a ratio for the two samples.

| | Amount (wt. %) | |
|---|---|---|
| | Broad | Preferred |
| Matrix | | |
| (1) Water-insoluble film former, e.g. Gantrez ® 225/425 (Agrimer ® VEMA ES 425) | 1–20 | 2–6 |
| (a) Optionally, a neutralizer, e.g. AMP | 0–20 neutralized | 0–10% neutralized |
| (2) Surfactant e.g. Igepal 630 | 1–25 | 2–16 |
| (a) Cosurfactant | | |
| e.g. Tagat I and/or | 0–25 | 0.2–2 |
| Gantrez ® M* | 0–20 | 0–6 |
| (3) Ethanol | 30–48 | 35–46 |
| (4) Water | 30–48 | 35–46 |
| Concentrate | | |
| Matrix | 90–99.5 | 95–99 |
| Sunscreen | 0.5–10 | 1–5 |
| Sunscreen Comp. | | |
| Concentrate | 1–100 | 10 |
| Water | 0–99 | 90 |

(3):(4) is about 1:1

*Tagat I is a 25EO glyceryl isostearate (Goldschmidt) and Gantrez ® M is polymethylvinyl ether (ISP); both are used with unneutralized film-former to assist solubilization.

Agrimer® VEMA ES type polymers are half-esters of alternating copolymers of an alkyl vinyl ether and maleic acid. Formulations were developed in ethanol/water medium, using methyl vinyl ether-monobutyl maleate copolymer as film-former, and insecticides and UV protectants as active ingredients.

Stable, water-based formulations containing high levels of water-insoluble UV protectants/insecticides are provided herein as sprayable microemulsions in the presence of film-forming Agrimer® VEMA ES 425 [methyl vinyl ether-maleic acid monobutyl ester]. Water-soluble Gantrez® M (polymethyl vinyl ether) polymer was useful in solubilizing Agrimer® VEMA ES 425 polymers in the acid form. Agrimer® VEMA ES polymers are soluble in alcohol and insoluble in water in the acid form. The solubility in a mixture of alcohol and water depends upon the relative amounts of alcohol/water, the extent of neutralization, temperature, and the chemical composition of the polymer (the nature of alkyl group, the extent of esterification, molecular weight, polydispersity, and the process parameters in the formation of the polymer). Solubilization of the polymer in alcohol/water medium was accomplished either by partial neutralization using bases such as 2-amino-2-methyl propanol (AMP) or by emulsification using appropriate emulsifiers. The most suitable emulsifiers were: alkylphenyl ethoxylates (Igepal® CO) and ethoxylated glyceryl isostearates (Tagat®). The active ingredients were also microemulsified in the same matrix by proper choice of emulsifiers.

Table 1 summarizes typical compositions for prototype formulations containing different levels of UV protectants in the presence of 4% film-forming polymer (Agrimer® VEMA ES 425). Table 2 summarizes the stability of the above compositions at room temperature, elevated temperature (45° C.), and sub-ambient temperature (3°–6° C.).

TABLE 1

Prototype Single Phase Compositions Containing Different Levels of UV Protectants

| Ingredients | Ex. Nos. and Compositions, weight % | | | | |
|---|---|---|---|---|---|
| | 1.1 | 1.2 | 1.3 | 1.4 | 1.5 |
| Agrimer ® VEMA ES 425 | 4.00 | 3.96 | 4.00 | 3.98 | 4.00 |
| AMP | 0.18 | 0.18 | 0.00 | 0.18 | 0.18 |
| Tagat ® I | 0.94 | 0.00 | 0.94 | 0.94 | 0.00 |
| Escalol ® 507 | 8.01 | 3.96 | 4.00 | 1.00 | 1.00 |
| Igepal ® CO 630 | 16.01 | 8.82 | 8.09 | 2.44 | 3.00 |
| Ethanol | 35.43 | 41.43 | 41.36 | 45.69 | 45.90 |
| Water | 35.43 | 41.65 | 41.62 | 45.77 | 45.92 |
| Total | 100.00 | 100.00 | 100.00 | 100.00 | 100.00 |

TABLE 2

Stability of Prototype Compositions of Table 1

| Appearance | Ex. Nos. and Compositions, weight % | | | | |
|---|---|---|---|---|---|
| | 1.1 | 1.2 | 1.3 | 1.4 | 1.5 |
| Room temperature, 25° C. | | | | | |
| Time: | | | | | |
| 0 | clear | clear | clear | clear | clear |
| 6 weeks | clear | clear | clear | clear | clear |
| Elevated temperature, 45° C. | | | | | |
| Time: | | | | | |
| 0 | clear | clear | clear | clear | clear |
| 6 weeks | clear | clear | clear | clear | clear |
| Sub-ambient temperature, 3–6° C., | | | | | |
| Time: | | | | | |
| 0 | clear | cloudy[1] | cloudy[1] | cloudy[1] | cloudy[1] |
| 6 weeks | clear | cloudy[1] | cloudy[1] | cloudy[1] | cloudy[1] |
| Dilution with deionized water, | | | | | |
| 1/10 | clear | clear | cloudy | clear | clear |
| 1/100 | clear | clear | hazy | clear | clear |

[1]Samples became clear and single phase when thawed to room temperature.

Table 3 summarizes typical single phase compositions containing piperonyl butoxide and D-allethrin as examples of insecticides in the presence of the film-forming polymer.

TABLE 3

Single Phase Compositions Containing Insecticides

| | Ex. Nos. and Compositions, weight % | |
|---|---|---|
| | 3.1 Piperonyl butoxide | 3.2 D-Allethrin |
| Ingredients | | |
| Agrimer ® VEMA ES 425 | 4.00 | 4.00 |
| AMP | 0.18 | 0.18 |
| Insecticide | 1.0 | 1.0 |
| Igepal ® CO 630 | 3.00 | 3.00 |
| Ethanol | 45.90 | 45.90 |
| Water | 45.92 | 45.92 |
| Total | 100.00 | 100.00 |
| Properties | | |
| Stability | — | — |
| Appearance, 0–16 days at Room temperature, 25° C. | clear | clear |
| Elevated temperature, 45° C. | clear | clear |
| Dilution with deionized water, 1/10 | clear | clear |

The formulations summarized in Table 1 did not separate on centrifugation for 30 minutes at 900 rpm, and on dilution at 1/10, and 1/100 with water. The diluted samples also did not separate after centrifugation for 30 minutes at 900 rpm. The concentrate was stable at 0°–45° C. on storage, monitored for 6 weeks. The compositions shown in Table 3 also did not separate when subjected to the above conditions. These results are indicative of the robustness of the compositions. Composition 1.5 contained the lowest level of total emulsifiers.

TABLE 4

Single Phase Matrix Compositions Containing Film-Forming Agrimer VEMA ES Polymers

| Ingredients | Ex. Nos. and Compositions, weight % | | | |
|---|---|---|---|---|
| | 4.1 | 4.2 | 4.3 | 4.4 |
| Agrimer ® VEMA ES 425 | 0.00 | 5.00 | 20.00 | 0.0 |
| Agrimer ® VEMA ES 225 | 20.00 | 0.00 | 0.00 | 2.00 |
| Gantrez ® M | 0.00 | 0.00 | 20.00 | 0.00 |
| AMP | 0.00 | 0.20 | 0.00 | 0.00 |
| Tagat ® I | 1.30 | 1.20 | 1.30 | 10.0 |
| Ethanol | 35.00 | 44.70 | 30.0 | 0.00 |
| Water | 43.70 | 48.90 | 28.70 | 88.0 |
| Total | 100.00 | 100.00 | 100.00 | 100.00 |

Table 4 shows typical single phase matrix compositions containing different levels of Agrimer® VEMA ES polymers. Agrimer® VEMA ES polymers in unneutralized form provide better adhesion on the skin/hair, because neutralization would provide negative charge on the polymer from the carboxylate anions that can produce repulsion from the residual negative charge on the skin/hair.

Solubilization of the Agrimer® ES polymers in the unneutralized form in aqueous or aqueous/alcoholic medium, however, is a challenging task. Agrimer® VEMA ES 425 in the unneutralized form can be solubilized in ~1:1 ethanol-water medium in the presence of polyvinyl methyl ether (Gantrez® M), and Tagat® I. (See Table 4). The role of Gantrez® M (a surface active polymer), in the solubilization may be explained as follows. Gantrez® M is surface active by virtue of a high order of tacticity in the polymer. The polymer is highly isotactic and the pendant groups are sufficiently small, further, the methoxy groups are polar, making it possible for the polymer to lay flat on the air/water or oil/water interface with methoxy groups aligned and pointing into the aqueous phase. Gantrez® M can form an intercoiled structure with Agrimer® VEMA ES 425. The complex will be more hydrophilic and easier to emulsify/solubilize in the aqueous phase. Agrimer® VEMA ES 225 in the unneutralized form can be solubilized in ~1:1 ethanol-water medium in the presence of Tagat® I (Table 4). Specific emulsifiers at certain minimum concentrations can solubilize the polymers (VEMA ES resins) in aqueous or aqueous-ethanol medium. In the partially neutralized forms VEMA ES resins required lower levels of specific emulsifiers to solubilize in aqueous or aqueous-ethanol medium. Compositions shown in Table 4 illustrate the above observations.

Example 4.4 illustrates the use of a specific emulsifier, Tagat I at a minimum concentration at emulsifier/polymer ratio=5.0 to solubilize the resin in water free from alcohol. Other compositions (4.1, 4.2, and 4.3) are in ethanol-water medium. The compositions shown in Table 4 can be used as matrices to load the appropriate active ingredients which are previously microemulsified in a similar solvent system with optimized emulsifiers. For example, it was found by an independent experiment that Igepal CO 630 (nonyl phenyl ethoxylate with 9 EO) solubilized Escalol 507 (octyl dimethyl PABA) in ~1:1 ethanol-water medium at a minimum concentration at surfactant/active ingredient ~2.0. An attempt to introduce the preemulsified Escalol 507 in the matrices 4.1, 4.2 and 4.3 produced single phase stable systems. Composition 1.1 in Table i is such an example [18 grams matrix 4.2 was mixed with 2 grams Escalol 507 and the mixture was titrated with Igepal CO 630 in small increments until the mixture became homogeneous, and the final composition was computed]. By a similar procedure mixed Escalol systems could also be microemulsified. The Escalol 507 (8 grams) in Example 1.1 can be replaced with a mixture of containing 6 grams Escalol 507 and 2 grams Escalol 567 (4,methoxy-2,hydroxy benzophenone). The composition containing mixed Escalols was also stable and produced single phase systems on dilution to ⅒ and ¹⁄₁₀₀ with deionized water. It was not possible to introduce Escalol 567 by itself in the matrix at a reasonable concentration, without using exorbitant levels of emulsifiers.

The benefit of the above type matrices and prototype compositions containing UV protectants and/or insecticides for animal use can be visualized as follows: microemulsified insecticides containing large proportion of emulsifiers in the presence of a film-forming polymer is expected to produce excellent wetting, spreading on hydrophobic surfaces. FIG. 3 shows comparative data on dynamic surface tension for the composition 1.5 and at ⅒ dilution along with Silwet L 77 (ethoxylated siloxanes). The dynamic surface tension of the samples derived from 1.5 are comparable or lower than those derived from Silwet L 77. Blank samples [a containing 3% Igepal CO 630 in 1:1 ethanol-water with no polymer present and b ⅒ dilution of a] produced similar profiles indicating that polymer migration to the surface does not adversely affect the speed of wetting.

Table 5 summarizes typical range of static surface tension, contact angle on a parafilm surface, of composition 1.5 at different dilutions and the Drave's wetting time for the matrix (composition 1.5 without the Escalol). The data in bold are for samples (composition 1.5) at different dilutions, that are representative of use levels of the matrices. Typical recommended dilution would be an equivalent of ⅒ of composition 1.5.

TABLE 5

Surface Properties of Water Compositions 1.5 and Diluted Samples Thereof

| Composition | Properties | | |
|---|---|---|---|
| | Static Surface tension, mN/M (±0.1) | Contact Angle, deg (±2) | Wetting time, sec (±5%) |
| Water | 70.35 | 104.3 | >>600 |
| Composition, 1.5 as is | 26.70 | 39.8 | 1.0 |
| Dilution Composition | | | |
| 1/10 | 30.30 | 54.9 | 7.4 |
| 1/50 | 31.30 | 52.6 | 40 |
| 1/100 Standard | 31.60 | 51.2 | 92 |
| Water-ethanol 1:1 | 26.70 | 58.7 | 1.0 |

While the invention has been described with particular reference to certain embodiments thereof, it will be understood that changes and modifications may be made which are within the skill of the art. Accordingly, it is intended to be bound only by the following claims, in which:

What is claimed is:

1. A matrix for a low VOC sunscreen spray and/or pesticide composition comprising, by weight,
   (a) a film-former, 1–20%, which is methyl vinyl ether-maleic acid monobutyl ester copolymer,
      (1) optionally neutralized up to 20%,
   (b) a surfactant, 1–30%, which is an alkyl phenyl ethoxylate,
      (1) optionally a cosurfactant, 0–30%, which is an ethoxylated glyceryl isostearate or poly(methyl vinyl ether),
   (c) ethanol, 30–48%, and
   (d) water, 30–48%,
wherein the weight ratio of (c):(d) is about 1:1.

2. A matrix according to claim 1 wherein
   (a) is 2–6%,
   (b) is 2–16%,
   (c) is 35–46%, and
   (d) is 35–46%.

3. A matrix according to claim 1 wherein (a) (1) is 5–10%; and (b) (1) is 0.2–10.

4.) A sunscreen and/or pesticide concentrate comprising:
   (a) 90–99.5% of the matrix of claim 1, and
   (b) 0.5–10% of a sunscreen and/or pesticide.

5. A sunscreen and/or pesticide composition comprising:
   (a) 1–100% of the concentrate of claim 4, and
   (b) 0–99% of water.

* * * * *